US006995140B1

(12) United States Patent
Meiniel et al.

(10) Patent No.: US 6,995,140 B1
(45) Date of Patent: Feb. 7, 2006

(54) PEPTIDES AND POLYPEPTIDES USEFUL FOR REGENERATING THE NERVOUS SYSTEM

(75) Inventors: Annie Meiniel, Cournon (FR); Hubert Monnerie, Roanne (FR); Stéphane Gobron, Clermont-Ferrand (FR)

(73) Assignees: NUCLEICA, Saint Beauzire (FR); Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 09/462,909

(22) PCT Filed: Jul. 16, 1998

(86) PCT No.: PCT/FR98/01556

§ 371 (c)(1),
(2), (4) Date: Feb. 14, 2000

(87) PCT Pub. No.: WO99/03890

PCT Pub. Date: Jan. 28, 1999

(30) Foreign Application Priority Data

Jul. 16, 1997 (FR) .................................. 97 09016

(51) Int. Cl.
*A61K 38/00* (2006.01)
*A01N 37/18* (2006.01)
*C07K 16/00* (2006.01)
*C12N 5/00* (2006.01)
*C12N 5/02* (2006.01)

(52) U.S. Cl. ........................... 514/13; 514/2; 530/324; 530/300; 530/322; 530/323; 435/375

(58) Field of Classification Search ................. 514/13, 514/2; 530/300, 350, 324, 322, 323; 436/86; 435/375

See application file for complete search history.

(56) References Cited

FOREIGN PATENT DOCUMENTS

| EP | 443 404 | 8/1991 |
| WO | 93/00430 | 1/1993 |
| WO | 94/06464 | 3/1994 |

OTHER PUBLICATIONS

Skolnick et al., 2000, Tibtech, vol. 18, pp. 34-49.*
Bork et al., 1998, Current Opinion in Structural Biology, vol. 8, pp. 331-332.*
Hoffer et al., 1997, J. Neural transm., vol. 49, pp. 1-10.*
A. Klar et al., "F.-Spondin" A Gene Expressed at High Levels . . . and Nuerite Extension, Cell, vol. 69, Apr. 1992, pp. 95-110, XP 002059005.
S. Gobron et al., "SCO-Spondin: a new member of the thrombospondin . . . of neuronal aggregation", J. of Cell Sci., 1996, pp. 1053-1061, XP 002059006.
G. Mor et al., "Induction of Neonatal Tolerance by Plasmid DNA Vaccination of Mice", J. Clinical Invest., vol. 98:12, Dec. 1996, pp. 2700-2705, XP 002084526.

* cited by examiner

*Primary Examiner*—Olga N. Chernyshev
(74) *Attorney, Agent, or Firm*—Foley & Lardner LLP

(57) ABSTRACT

The invention concerns in particular novel peptides and polypeptides comprising at least the following sequence in amino acids: -W-S-A1-C-S-A2-C-G- in which A1 and A2 are amino acid sequences comprising 1 to 5 amino acids, useful as medicines in therapeutic treatments involving the regeneration of the nervous system cells, for treating neuroblastomas, and also useful as additives in the culture of nervous cells.

16 Claims, 2 Drawing Sheets

Figure 1:

Photomicrographs from sagittal spinal cord section at the lesion site where the collagen tube (star) was inserted. The immunodetection of Neurofilament (NF), performed on control rats (A, B) revealed the absence of nerve fibers and connective tissue within the collagen channel (Star) from both rostal (r) and caudal (c) stumps of the lesioned spinal cord.

Figure 2

Neurofilament-immunopositive fibers growing within a collagen tube containing pep1 from the rostral (A) as well as the caudal (B) border of the spinal lesion. As indicated by the white arrow, nerve fibers were able to regenerate up to 2 mm into the collagen channel 10 days after surgery. High magnification of a NF-positive nerve fibers (C) pointed out in A with the white arrow. Scale bars: A, B: 250 mm.

PEPTIDES AND POLYPEPTIDES USEFUL FOR REGENERATING THE NERVOUS SYSTEM

This application claims priority to French Application 97-0916 filed on Jul. 16, 1997 and international application PCT/FR98/01556, filed on Jul. 16, 1998, designating the United States of America, and published on Jan. 28, 1999, in the French language in accordance with PCT Article 21(2) as WO 99/03890.

The present invention relates in particular to novel peptides and polypeptides useful in particular as medicines in therapeutic treatments involving the regeneration of the nervous system cells, for treating neuroblastomas, and also useful as additives in the cultures of nerve cells.

Many proteins comprising repeating units which are called thrombospondin type I units (TSRs) have been identified during the past few years. It can be said that these proteins have highly varied activities depending on the biological system in which they are involved. There may be mentioned, as the best studied and therefore the best known examples, the CS proteins (of circumsporozoite) which allow binding to the hepatic cells of the agent for the propagation of malaria, the *plasmodium falciparum* sporozoite (WO 94/06646) and the thrombospondin secreted by the blood platelets which are involved in the phenomena of thrombosis and angiogenesis (EP 443 404).

In fact, this thrombospondin type 1 unit (TSR) comprises, in all the proteins studied so far and previously mentioned, about 60 amino acids (AA) some of which, like cysteines (C), tryptophans (W), serines (S), glycines (G), arginines (R) and prolines (P) are highly conserved (see below the alignment of these conserved AAs in a few proteins).

Some synthetic peptides, deduced from these TSR units, have valuable biological properties. Thus, the CSVTCG (SEQ ID NO:21) units allow the adhesion of the *plasmodium* sporozoites to the hepatic cells, the CSVTCG (SEQ ID NO:21) and WXXW (SEQ ID NO:22) units allow cellular attachment in other biological models, BBXB (SEQ ID NO:23) (B being a basic amino acid) binds heparin and finally WSXWS (SEQ ID NO:24) binds certain growth factors.

F-spondin has been described and its sequence has been aligned with that of thrombospondin in Klar et al., (1992), Cell, 69, 95–110.

The general characteristics of SCO-spondin are described in particular in the article by Monnerie et al. (submitted) and the article by Gobron et al., (1996), Journal of Cell Science, 109, 1053–1061, 1996. In particular, the alignment of the sequence of SCO-spondin has revealed homologies with proteins such as thrombospondin 1 and 2 (see sequence, alignment page 1057 of Gobron et al., (1996), J. of Cell Science 109, 1053–1061, incorporated into the description by reference).

The novelty of the present invention consists in the identification and the selection of a novel peptide which is active in the regeneration of the nervous system, whose sequence is derived from one of the TSRs of SCO-spondin.

More particularly, the present invention relates to a peptide or polypeptide having the formula:

-W-S-$A_1$-C-S-$A_2$-C-G- (SEQ ID NOS: 1 and 25–49)

in which $A_1$ and $A_2$ are amino acid sequences comprising 1 to 5 amino acids, with the exception of the peptides or polypeptides having one of the following sequences

-W-S-P-C-S-V-T-C-G- (SEQ ID NO: 2)

-W-S-S-C-S-V-T-C-G- (SEQ ID NO: 3)

-W-S-Q-C-S-V-T-C-G- (SEQ ID NO: 4)

It should be recalled that in the description as a whole, "amino acid" is understood to mean both the natural amino acids and the non-natural amino acids. "Natural amino acid" is understood to mean the amino acids in the L form which can be found in natural proteins, that is to say alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. However, the present invention also relates to the non-natural amino acids, that is to say the preceding amino acids in their D form, as well as the homo forms of some amino acids such as arginine, lysine, phenylalanine and serine or the nor forms of leucine or valine.

It is also possible to envisage using other amino acids such as, for example:

| | |
|---|---|
| Abu: | alpha-aminobutyric acid |
| Agm: | agmatine |
| Aib: | alpha-aminoisobutyric acid |
| F-trp: | N-formyl-trp | sarcosine
statine
ornithine
desaminotyrosine.

Desaminotyrosine is incorporated at the N-terminal end whereas agmatine and statin are incorporated at the C-terminal end of these peptides.

Preferably, the peptides according to the present invention $A_1$ is proline or $X_1$-W-$X_2$-$X_3$ (SEQ ID NOS: 5 and 50–59) where $X_1$, $X_2$, $X_3$ are chosen, independently of each other, from G, S and C, that is to say small amino acids.

Still preferably, $A_1$ is $X_1$-W-S-$X_3$ (SEQ ID NOS: 6 and 60–64) and $A_2$ is chosen from RS, VS and VT.

The reasons for these choices will emerge on reading some examples.

Preferably, the polypeptide according to the present invention has the following structure:

-W-S—$X_1$-W-S-$X_2$-C-S-$A_2$-C-G- (SEQ ID NOS: 7 and 89–96)

The preferred peptide has the following structure:

-W-S-G-W-S-S-C-S-R-S-C-G- (SEQ ID NO: 8)

Preferably, the peptides and polypeptides according to the present invention will have the following structure:

Y-W-S-$A_1$-C-S-$A_2$-C-G-Z (SEQ ID NOS: 9 and 97–168)

in which Y and Z constitute the N- and C-terminal ends of the peptide, or comprise amino acid chains having less than 6 amino acids, or comprise chains of compounds which are not amino acids.

This corresponds to the peptide per se or to a peptide in which the Z and Y ends enhance the pharmacological activity or ensure a better penetration or bioavailability of the active ingredient; thus, it is possible to envisage in the Y and Z ends the use of hydrophilic components which make it possible, where appropriate, to cross certain biological barriers, or alternatively, on the contrary, to envisage more hydrophilic sequences which will allow a better solubilization of the products involved.

Finally, the modification of the ends can facilitate the incorporation of these products into particular galenic forms such as, for example, liposomes or microparticles.

The present invention also relates to DNA expression vectors characterized in that they are capable of expressing the preceding peptides or polypeptides.

The DNA sequences encoding the preceding peptides or polypeptides can be easily determined from amino acid sequences or based, for example, on the natural sequences as will be described in the present application.

The vectors for administration may consist of naked DNA vectors, plasmid vectors, viral vectors or alternatively synthetic vectors.

These are known technologies which will not be described in detail.

The use of these expression vectors makes it possible to express in situ the peptides or polypeptides involved and, in some cases, is likely to enhance their activity.

Constructs will of course be chosen which exhibit, if possible, specificity for the nerve cells, since they are the preferred targets for the polypeptides according to the present invention.

The peptides and polypeptides according to the present invention may be prepared by any appropriate method, in particular they may be obtained by chemical synthesis, but it is also possible to obtain them by the biological route using in particular the vectors mentioned above in appropriate cell cultures.

It should in fact be noted, in this regard, that the polypeptides and peptides according to the present invention may be provided in deglycosylated or glycosylated form if necessary. It should also be noted that in some cases and depending on the method of preparation, it may be necessary to renature some tertiary structures of the peptide.

Finally, the polypeptides according to the present invention can be more particularly used for the manufacture of a medicine with the aim of being administered in vivo, in particular in all pathological conditions and traumas requiring regeneration of the nervous system cells, and more particularly of their outgrowths and synapses.

These may be pathological conditions or traumas in which neurodegeneration is observed, but they may also be pathological conditions or traumas in which the regeneration of the central nervous system, in particular of the axons, or of the peripheral nerves is necessary.

Among the neurodegenerative pathological conditions in which the compounds according to the present invention may provide a support, there may be mentioned in particular Alzheimer's disease, multiple sclerosis, Parkinson's disease and the different types of myopathies.

As regards the regeneration of the neuronal outgrowths, in particular of the axons, this may involve in particular accident- or trauma-type problems (section of the spinal cord or of the peripheral nerves).

Likewise, the compounds according to the present invention may be used as additives in certain cell cultures with the same effects as those mentioned above on the growth of cells.

More particularly, the compounds according to the present invention increase neuritic growth (including the axons) in the cerebral cortex neurons. Inhibition of aggregation and defasciculation of the neurites are noted on the spinal cord neurons and an increase in synaptic contacts is also noted.

"Neuritic growth" is defined as an extension, that is to say growth of the neuron outgrowths, whether the dendritic or axonal outgrowth.

"Aggregation" is defined as a grouping together of the cells forming a cluster.

"Defasciculation" is defined as the result of a decrease in adhesivity between neurites, leading to a loose network of neuronal outgrowths.

"Synaptic contact" is defined as the capacity for a neuronal cell to communicate with another cell, it being possible for the latter to also be neuronal.

In another aspect of the present invention, said peptides or polypeptides may be useful for inducing regression of tumorigenicity during a neuroblastoma.

The nomenclature used to describe the sequence of the present peptide is the international nomenclature using the three-letter code or the one-letter code and where the amino-terminal end is presented on the left and the carboxy-terminal end is presented on the right.

The compositions according to the present invention may be provided in any customary form for pharmaceutical administration, that is to say for example forms for liquid administration in a gel or any other support allowing, for example, controlled release.

Among the compositions which may be used, there should be mentioned in particular the injectable compositions more particularly intended for injections into the meningeal and subarachnoidal spaces.

The most active peptide according to the present invention has the following formula:

Trp-Ser-Gly-Trp-Ser-Ser-Cys-Ser-Arg-Ser-Cys-Gly
(SEQ ID NO: 8)

It is soluble in basic aqueous medium, has a molecular weight of 1301 Da and has an amino acid composition of:

|   |     |            | N | N (%) | MW  | MW (%) |
|---|-----|------------|---|-------|-----|--------|
| C | Cys | Cysteine   | 2 | 16.7  | 206 | 15.8   |
| G | Gly | Glycine    | 2 | 16.7  | 114 | 8.8    |
| R | Arg | Arginine   | 1 | 8.3   | 156 | 12.0   |
| S | Ser | Serine     | 5 | 41.7  | 435 | 33.4   |
| W | Trp | Tryptophan | 2 | 16.7  | 372 | 28.6   |

It was obtained by solid phase chemical synthesis.

However, as was indicated above, it can be obtained by genetic engineering using a host-vector system comprising DNA encoding the peptide taking into account, for example, the degeneracy so as to produce it in a large quantity.

The cDNA sequence encoding the peptide may be 20 presented in the following manner (SEQ ID NO: 10):

```
5' TGG WSN GGN TGG WSN WSN TGY WSN MGN WSN TGY
GGN 3'
A = Adenosine      W = A or T
C = Cytosine       S = G or C
G = Guanosine      Y = C or T
T = Thymidine      M = A or C
N = A, C, G or T
```

The peptide thus obtained was identified by microsequencing, HPLC analysis, mass spectrometry and sequencing of the complementary DNA.

It is on this peptide (SEQ ID NO: 8) that the experiments described below were carried out.

EXAMPLE 1

Effect of the Peptide SEQ ID NO: 8 on the Growth of the Neurons

Materials and Method

Dissociated Cell Cultures of Cerebral Hemispheres of 8-Day Old Chicken Embryos

The neuronal cultures are obtained from 8-day old chicken embryos. The cerebral hemispheres, after removing the meninges, are cut into small pieces and enzymatically dissociated with 0.25% of trypsin in a PBS saline buffer free of calcium and of magnesium for 15 minutes at 37° C.

The cells are centrifuged at 200 g for 5 minutes in DMEM medium with 20% FCS for the trypsin inactivation. The cells are then filtered on nylon membrane (pore size: 48 microns) and collected in a chemically defined medium free of serum containing a 1/1 mixture of DMEM and Ham's F12 medium supplemented with glutamine (4 mM), glucose (33 mM), penicillin G (50 U/ml), streptomycin sulfate (50 µg/ml) and an N2 supplement of Bottenstein and Sato (1979): putrescine (100 µM), sodium selenite (30 nM), human transferrin (50 µg/ml), progesterone (20 nM), insulin (5 µg/ml) and β-estradiol (1 pM). All the N2 supplements were bought from Sigma.

The cells are plated at a density of $7.5 \times 10^4$ cells/cm$^2$ on 24-well plastic plates. For some experiments, the plastic plates are coated either with fibronectin (24 µg/ml) or with thrombospondin (20 µg/ml). The cultures are incubated at 37° C. and under air containing 10% $CO_2$. The medium is not changed during the experiment. These cultures consist of nearly 95% of neurons.

Cell Cultures of Spinal Neurons

The spinal cords of 6-day old chicken embryos are dissected, freed of their meningeal membrane and cut into small pieces in a phosphate buffer (PBS) free of calcium and of magnesium. After incubation with 0.25% trypsin for 10 minutes at 37° C., the tissue is centrifuged at 200 g for 4 minutes in a growth medium containing 20% fetal calf serum in order to stop the trypsinization. The cells are then dissociated by repeated trituration using a Pasteur pipette and resuspended in a chemically defined medium free of serum as above.

The cells are plated at a density of $7.5 \times 10^4$ cells/cm$^2$ on 24-well plastic culture plates. The cultures are incubated at 37° C. and under air containing 10% $CO_2$. The medium is not changed during the experiments and it has already been shown that this type of cell population contained more than 93% of neurons.

The peptides tested are, in addition to the peptide according to the present invention mentioned above (peptide SEQ ID NO: 8), a second peptide according to the invention having the structure:

W-G-P-C-S-V-S-C-G- (SEQ ID NO: 11)

then 3 peptides for comparison:

D-C-K-D-G-S-D-E- (SEQ ID NO: 12)

R-K-A-R- (SEQ ID NO: 13)

and a mixed sequence of the peptide SEQ ID NO: 8:

S-S-C-R-S-G-C-W-G-S-S-W- (SEQ ID NO: 14).

All these peptides were obtained by synthesis.

Results

In the presence of the peptide SEQ ID NO: 8, the neurons aggregate and are essentially connected by bundles of long and thick neurites after 5 days of culture. Furthermore, these cells adhere well to the substrate coated with the peptide with no detachment of the aggregates. By contrast, the control cell cultures, in the absence of the peptide, rapidly detach from the plastic substrate at 5 days of culture. However, on plastic, only the cortical neurons form aggregates from which very few neurites can be observed, which indicates that the substrate is insufficiently adhesive. The number of neuronal aggregates increases by 9.3% between the control culture and the culture treated with the peptide according to the invention.

Morphometric analysis reveals a significant increase both in the number of neurites per aggregate and in the length of the neurites per aggregate. Moreover, wells of plastic coated with BSA are only very slightly adhesive for the neuronal cells.

The tests carried out with other peptides in comparison with the peptide SEQ ID NO: 8 at random give no significant result.

The peptide SEQ ID NO: 11 gives lower but, nevertheless, significant results.

Likewise, the tests carried out with the peptide SEQ ID NO: 13, which is a consensus sequence for attachment of glycosaminoglycans which is present in a large number of proteins which bind to heparin, as well as the peptides corresponding to type A LDL receptors, gave no representative result.

Moreover, the effect of the peptides according to the present invention SEQ ID NO: 8 and NO: 11 on cultures at low density was studied. Indeed, it has already been demonstrated that high aggregation could influence neuritic growth in the same manner as the strength of adhesion of the cells to the substrate.

The tests carried out at low density showed that in the absence of aggregation, the two peptides significantly increased the percentage of neuronal cells carrying neurites. In the controls, only 24.4% of the adherent cells had neurites at 4 days of culture whereas 2 and 2.5 times as many appeared in the presence of the peptides SEQ ID NO: 8 and NO: 11, respectively.

The morphometric analyses revealed a significant increase in each of them both in the number of neurites per cell and the length of the neurites in the presence of the peptide SEQ ID NO: 8 and not the peptide SEQ ID NO: 11. Under these conditions, this demonstrates that, even in the absence of neuronal. aggregation, the peptide SEQ ID NO: 8 and to a lesser degree the peptide SEQ ID NO: 11 are capable of promoting the adhesion and the neuritic growth of the cortical neuronal cells.

The effect of the peptide SEQ ID NO: 8 of the invention was also studied under various experimental conditions:

In the presence of various substrates, it was possible to demonstrate, for example, that the peptide according to the invention significantly increased the number of neurites per aggregate in well-containing plates coated with thrombospondin and fibronectin, compared with the controls, as well as the length of the neurites per aggregate.

The activity of the peptide SEQ ID NO: 8 on the spinal cord cell cultures compared with controls shows that the neurons remain distributed for at least one week in vitro. The neurons show prominent neuritic growths forming a network without fasciculation of the neurites. An increase in the number of synaptic contacts between the neurites is observed. By contrast, the neuronal cells of the controls form, in general, small aggregates interconnected by long filaments. The neurites growing from the aggregates form relatively rigid bundles along which essentially simple, bi- or tripolar neurons can be seen.

The other peptides tested under the same conditions show no notable difference compared with the controls.

EXAMPLE 2

Effect of the Peptide SEQ ID NO: 8 on the Neuroblastoma Derived from NIB104

Materials and Method

The cells derived from the NIB104 neuroblastoma were cultured in 24-well plastic plates previously coated with a film of poly-L-lysine, under conditions similar to those for the primary cultures.

Results

In the presence of the peptide SEQ ID NO: 8 according to the present invention, the NIB104 neuroblastoma cells are considerably less numerous than in the control cultures. The appearance of the cells is considerably modified because they acquire a characteristic neuronal phenotype. Morphometric analysis reveals that in the presence of increasing concentrations of peptide in the culture medium, the neuritic growth gradually increases. This response is therefore dose-dependant and indicative of a specific physiological effect.

What is claimed is:

1. A composition comprising the peptide:

Y-W-S-$A_1$-C-S-$A_2$-C-G-Z(SEQ ID NO: 9)

wherein Y and Z consist of:

(a) amino acid chains consisting of 0–6 amino acids; or (b) chains of compounds which are not amino acids, wherein $A_1$ and $A_2$ are amino acid sequences consisting of 1 to 5 amino acids and further wherein the peptide is not selected from the group consisting of one of the following sequences:

-W-S-P-C-S-V-T-C-G- (SEQ ID NO:2),

-W-S-S-C-S-V-T-C-G- (SEQ ID NO:3), and

-W-S-Q-C-S-V-T-C-G- (SEQ ID NO:4).

2. The composition according to claim 1, wherein said $A_1$ is Pro or -$X_1$-W-$X_2$-$X_3$-(SEQ ID NO:5).

3. The composition according to claim 2, wherein said $A_1$ is -$X_1$-W-S-$X_3$-(SEQ ID NO:6).

4. The composition according to claim 1, wherein said $A_2$ is selected from the group consisting of -R-S-, -V-S-, and -V-T-.

5. The composition according to claim 3, wherein said peptide is -W-S-$X_1$-W-S-$X_3$-C-S- $A_2$-C-G- (SEQ ID NO:7).

6. The composition according to claim 4, wherein said peptide is:

-W-S-G-W-S-S-C-S-R-S-C-G- (SEQ ID NO:8).

7. A composition comprising a peptide according to claim 1 and a pharmaceutically acceptable vehicle.

8. An additive for culturing nerve cells, comprising a peptide according to claim 1.

9. A composition according to claim 1, wherein the peptide is selected from the group consisting of SEQ ID NOS: 97–168.

10. A composition according to claim 2, wherein the peptide is selected from the group consisting of SEQ ID NOS: 50–59.

11. A composition according to claim 3, wherein the peptide is selected from the group consisting of SEQ ID NOS: 60–64.

12. A composition according to claim 4, wherein the peptide is selected from the group consisting of SEQ ID NOS: 65–88.

13. A composition according to claim 5, wherein the peptide is selected from the group consisting of SEQ ID NOS: 89–96.

14. A peptide consisting of the following amino acid sequence:

-W-S-G-W-S-S-C-S-R-S-C-G- (SEQ ID NO:8).

15. A composition comprising a peptide according to claim 14 and a pharmaceutically acceptable vehicle.

16. An additive for culturing nerve cells, comprising a peptide according to claim 14.

* * * * *

SEQUENCE LISTING

```
<160> NUMBER OF SEQ ID NOS: 168

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid; this range may encompass 1-5
      amino acids
<220> FEATURE:
<221> NAME/KEY: MOD_RES
<222> LOCATION: (10)..(14)
<223> OTHER INFORMATION: Any amino acid; this range may encompass 1-5
      amino acids

<400> SEQUENCE: 1

Trp Ser Xaa Xaa Xaa Xaa Xaa Cys Ser Xaa Xaa Xaa Xaa Xaa Cys Gly
 1               5                  10                  15

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ser Pro Cys Ser Val Thr Cys Gly
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Ser Ser Cys Ser Val Thr Cys Gly
 1               5

<210> SEQ ID NO 4
<211> LENGTH: 9
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Ser Gln Cys Ser Val Thr Cys Gly
  1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Gly, Ser or Cys
<220> FEATURE:
<221> NAME/KEY: MOD_RES
<222> LOCATION: (3)..(4)
<223> OTHER INFORMATION: Gly, Ser or Cys

<400> SEQUENCE: 5

Xaa Trp Xaa Xaa
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Gly, Ser or Cys
<220> FEATURE:
<221> NAME/KEY: MOD_RES
<222> LOCATION: (4)
<223> OTHER INFORMATION: Gly, Ser or Cys

<400> SEQUENCE: 6

Xaa Trp Ser Xaa
  1

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Formula
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)..(10)
<223> OTHER INFORMATION: Arg Ser, Val Ser or Val Thr

<400> SEQUENCE: 7

Trp Ser Xaa Trp Ser Xaa Cys Ser Xaa Xaa Cys Gly
```

-continued

```
                1               5                    10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ser Gly Trp Ser Ser Cys Ser Arg Ser Cys Gly
  1               5                    10

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Formula
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Pro, Gly, Ser or Cys
<220> FEATURE:
<221> NAME/KEY: MOD_RES
<222> LOCATION: (9)
<223> OTHER INFORMATION: Not present if residue 8 is Pro; this residue
      is Trp if residue 8 is Gly, Ser or Cys
<220> FEATURE:
<221> NAME/KEY: MOD_RES
<222> LOCATION: (10)..(11)
<223> OTHER INFORMATION: Not present if residue 8 is Pro; these residues
      are selected from Gly, Ser or Cys if residue 8 is
      Gly, Ser or Cys
<220> FEATURE:
<221> NAME/KEY: MOD_RES
<222> LOCATION: (14)..(15)
<223> OTHER INFORMATION: Arg Ser, Val Ser or Val Thr
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 9

Xaa Xaa Xaa Xaa Xaa Trp Ser Xaa Xaa Xaa Xaa Cys Ser Xaa Xaa Cys
  1               5                    10                  15

Gly Xaa Xaa Xaa Xaa Xaa
            20

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: a, t, c or g
<220> FEATURE:
<221> NAME/KEY: modified_base
<222> LOCATION: (9)
<223> OTHER INFORMATION: a, t, c or g
<220> FEATURE:
```

```
<221> NAME/KEY: modified_base
<222> LOCATION: (15)
<223> OTHER INFORMATION: a, t, c or g
<220> FEATURE:
<221> NAME/KEY: modified_base
<222> LOCATION: (18)
<223> OTHER INFORMATION: a, t, c or g
<220> FEATURE:
<221> NAME/KEY: modified_base
<222> LOCATION: (24)
<223> OTHER INFORMATION: a, t, c or g
<220> FEATURE:
<221> NAME/KEY: modified_base
<222> LOCATION: (27)
<223> OTHER INFORMATION: a, t, c or g
<220> FEATURE:
<221> NAME/KEY: modified_base
<222> LOCATION: (30)
<223> OTHER INFORMATION: a, t, c or g
<220> FEATURE:
<221> NAME/KEY: modified_base
<222> LOCATION: (36)
<223> OTHER INFORMATION: a, t, c or g

<400> SEQUENCE: 10
tggwsnggnt ggwsnwsntg ywsnmgnwsn tgyggn                                   36

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Gly Pro Cys Ser Val Ser Cys Gly
  1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Cys Lys Asp Gly Ser Asp Glu
  1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Lys Ala Arg
  1

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Ser Ser Cys Arg Ser Gly Cys Trp Gly Ser Ser Trp
  1               5                  10

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Ser Pro Trp Ser Glu Trp Thr Ser Cys Ser Thr Ser Cys Gly Asn
  1               5                  10                  15

Gly Ile Gln Gln Arg Gly Arg
             20

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ser His Trp Ser Pro Trp Ser Ser Cys Ser Val Thr Cys Gly Asp
  1               5                  10                  15

Gly Val Ile Thr Arg Ile Arg
             20

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Gly Pro Trp Ser Pro Trp Asp Ile Cys Ser Val Thr Cys Gly Gly
  1               5                  10                  15

Gly Val Gln Lys Arg Ser Arg
             20

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Ser Gln Cys Ser Val Tyr Cys Gly
  1               5

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 19

Thr Glu Trp Ser Ala Cys Ser Lys Ser Cys Gly Met Gly Phe Ser Thr
 1               5                  10                  15

Arg Val Thr Asn Arg Asn
             20

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Glu Trp Ser Ala Cys Ser Lys Thr Cys Gly Met Gly Ile Ser Thr
 1               5                  10                  15

Arg Val Thr Asn Asp Asn
             20

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Ser Val Thr Cys Gly
 1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 22

Trp Xaa Xaa Trp
 1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any basic amino acid
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (4)
<223> OTHER INFORMATION: Any basic amino acid

<400> SEQUENCE: 23
```

```
Xaa Xaa Xaa Xaa
  1

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Any amino acid

<400> SEQUENCE: 24

Trp Ser Xaa Trp Ser
  1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (6)
<223> OTHER INFORMATION: Any amino acid

<400> SEQUENCE: 25

Trp Ser Xaa Cys Ser Xaa Cys Gly
  1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 26

Trp Ser Xaa Cys Ser Xaa Xaa Cys Gly
  1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Any amino acid
<220> FEATURE:
```

```
<221> NAME/KEY: MOD_RES
<222> LOCATION: (6)..(8)
<223> OTHER INFORMATION: Any amino acid

<400> SEQUENCE: 27

Trp Ser Xaa Cys Ser Xaa Xaa Xaa Cys Gly
 1               5                  10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (6)..(9)
<223> OTHER INFORMATION: Any amino acid

<400> SEQUENCE: 28

Trp Ser Xaa Cys Ser Xaa Xaa Xaa Xaa Cys Gly
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (6)..(10)
<223> OTHER INFORMATION: Any amino acid

<400> SEQUENCE: 29

Trp Ser Xaa Cys Ser Xaa Xaa Xaa Xaa Xaa Cys Gly
 1               5                  10

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (7)
<223> OTHER INFORMATION: Any amino acid

<400> SEQUENCE: 30

Trp Ser Xaa Xaa Cys Ser Xaa Cys Gly
 1               5

<210> SEQ ID NO 31
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 31

Trp Ser Xaa Xaa Cys Ser Xaa Xaa Cys Gly
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (7)..(9)
<223> OTHER INFORMATION: Any amino acid

<400> SEQUENCE: 32

Trp Ser Xaa Xaa Cys Ser Xaa Xaa Xaa Cys Gly
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (7)..(10)
<223> OTHER INFORMATION: Any amino acid

<400> SEQUENCE: 33

Trp Ser Xaa Xaa Cys Ser Xaa Xaa Xaa Xaa Cys Gly
 1               5                  10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (7)..(11)
<223> OTHER INFORMATION: Any amino acid
```

<400> SEQUENCE: 34

Trp Ser Xaa Xaa Cys Ser Xaa Xaa Xaa Xaa Xaa Cys Gly
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (8)
<223> OTHER INFORMATION: Any amino acid

<400> SEQUENCE: 35

Trp Ser Xaa Xaa Xaa Cys Ser Xaa Cys Gly
 1               5                  10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid

<400> SEQUENCE: 36

Trp Ser Xaa Xaa Xaa Cys Ser Xaa Xaa Cys Gly
 1               5                  10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (8)..(10)
<223> OTHER INFORMATION: Any amino acid

<400> SEQUENCE: 37

Trp Ser Xaa Xaa Xaa Cys Ser Xaa Xaa Xaa Cys Gly
 1               5                  10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (8)..(11)
<223> OTHER INFORMATION: Any amino acid

<400> SEQUENCE: 38

Trp Ser Xaa Xaa Xaa Cys Ser Xaa Xaa Xaa Xaa Cys Gly
 1               5                  10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (8)..(12)
<223> OTHER INFORMATION: Any amino acid

<400> SEQUENCE: 39

Trp Ser Xaa Xaa Xaa Cys Ser Xaa Xaa Xaa Xaa Xaa Cys Gly
 1               5                  10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (9)
<223> OTHER INFORMATION: Any amino acid

<400> SEQUENCE: 40

Trp Ser Xaa Xaa Xaa Xaa Cys Ser Xaa Cys Gly
 1               5                  10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (9)..(10)
<223> OTHER INFORMATION: Any amino acid

<400> SEQUENCE: 41

Trp Ser Xaa Xaa Xaa Xaa Cys Ser Xaa Xaa Cys Gly
 1               5                  10
```

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (9)..(11)
<223> OTHER INFORMATION: Any amino acid

<400> SEQUENCE: 42

Trp Ser Xaa Xaa Xaa Xaa Cys Ser Xaa Xaa Xaa Cys Gly
 1               5                  10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (9)..(12)
<223> OTHER INFORMATION: Any amino acid

<400> SEQUENCE: 43

Trp Ser Xaa Xaa Xaa Xaa Cys Ser Xaa Xaa Xaa Xaa Cys Gly
 1               5                  10

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (9)..(13)
<223> OTHER INFORMATION: Any amino acid

<400> SEQUENCE: 44

Trp Ser Xaa Xaa Xaa Xaa Cys Ser Xaa Xaa Xaa Xaa Xaa Cys Gly
 1               5                  10                  15

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid -continued

```
<220> FEATURE:
<221> NAME/KEY: MOD_RES
<222> LOCATION: (10)
<223> OTHER INFORMATION: Any amino acid

<400> SEQUENCE: 45

Trp Ser Xaa Xaa Xaa Xaa Cys Ser Xaa Cys Gly
 1               5                  10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid
<220> FEATURE:
<221> NAME/KEY: MOD_RES
<222> LOCATION: (10)..(11)
<223> OTHER INFORMATION: Any amino acid

<400> SEQUENCE: 46

Trp Ser Xaa Xaa Xaa Xaa Xaa Cys Ser Xaa Xaa Cys Gly
 1               5                  10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid
<220> FEATURE:
<221> NAME/KEY: MOD_RES
<222> LOCATION: (10)..(12)
<223> OTHER INFORMATION: Any amino acid

<400> SEQUENCE: 47

Trp Ser Xaa Xaa Xaa Xaa Xaa Cys Ser Xaa Xaa Xaa Cys Gly
 1               5                  10

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid
<220> FEATURE:
<221> NAME/KEY: MOD_RES
<222> LOCATION: (10)..(13)
<223> OTHER INFORMATION: Any amino acid

<400> SEQUENCE: 48

Trp Ser Xaa Xaa Xaa Xaa Xaa Cys Ser Xaa Xaa Xaa Xaa Cys Gly
 1               5                  10                  15

<210> SEQ ID NO 49
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid
<220> FEATURE:
<221> NAME/KEY: MOD_RES
<222> LOCATION: (10)..(14)
<223> OTHER INFORMATION: Any amino acid

<400> SEQUENCE: 49

Trp Ser Xaa Xaa Xaa Xaa Xaa Cys Ser Xaa Xaa Xaa Xaa Xaa Cys Gly
 1               5                  10                  15

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (5)..(6)
<223> OTHER INFORMATION: Gly, Ser or Cys
<220> FEATURE:
<221> NAME/KEY: MOD_RES
<222> LOCATION: (9)
<223> OTHER INFORMATION: Any amino acid

<400> SEQUENCE: 50

Trp Ser Xaa Trp Xaa Xaa Cys Ser Xaa Cys Gly
 1               5                  10

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Any amino acid

<400> SEQUENCE: 51

Trp Ser Pro Cys Ser Xaa Cys Gly
 1               5

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (5)..(6)
<223> OTHER INFORMATION: Gly, Ser or Cys
```

```
<220> FEATURE:
<221> NAME/KEY: MOD_RES
<222> LOCATION: (9)..(10)
<223> OTHER INFORMATION: Any amino acid

<400> SEQUENCE: 52

Trp Ser Xaa Trp Xaa Xaa Cys Ser Xaa Xaa Cys Gly
 1               5                  10

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Any amino acid

<400> SEQUENCE: 53

Trp Ser Pro Cys Ser Xaa Xaa Cys Gly
 1               5

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (5)..(6)
<223> OTHER INFORMATION: Gly, Ser or Cys
<220> FEATURE:
<221> NAME/KEY: MOD_RES
<222> LOCATION: (9)..(11)
<223> OTHER INFORMATION: Any amino acid

<400> SEQUENCE: 54

Trp Ser Xaa Trp Xaa Xaa Cys Ser Xaa Xaa Xaa Cys Gly
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(8)
<223> OTHER INFORMATION: Any amino acid

<400> SEQUENCE: 55

Trp Ser Pro Cys Ser Xaa Xaa Xaa Cys Gly
 1               5                  10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
          peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (5)..(6)
<223> OTHER INFORMATION: Gly, Ser or Cys
<220> FEATURE:
<221> NAME/KEY: MOD_RES
<222> LOCATION: (9)..(12)
<223> OTHER INFORMATION: Any amino acid

<400> SEQUENCE: 56

Trp Ser Xaa Trp Xaa Xaa Cys Ser Xaa Xaa Xaa Xaa Cys Gly
  1               5                  10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(9)
<223> OTHER INFORMATION: Any amino acid

<400> SEQUENCE: 57

Trp Ser Pro Cys Ser Xaa Xaa Xaa Xaa Cys Gly
  1               5                  10

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (5)..(6)
<223> OTHER INFORMATION: Gly, Ser or Cys
<220> FEATURE:
<221> NAME/KEY: MOD_RES
<222> LOCATION: (9)..(13)
<223> OTHER INFORMATION: Any amino acid

<400> SEQUENCE: 58

Trp Ser Xaa Trp Xaa Xaa Cys Ser Xaa Xaa Xaa Xaa Xaa Cys Gly
  1               5                  10                  15

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(10)
<223> OTHER INFORMATION: Any amino acid

<400> SEQUENCE: 59

Trp Ser Pro Cys Ser Xaa Xaa Xaa Xaa Xaa Cys Gly
```

```
                 1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)
<223> OTHER INFORMATION: Any amino acid

<400> SEQUENCE: 60

Trp Ser Xaa Trp Ser Xaa Cys Ser Xaa Cys Gly
  1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)..(10)
<223> OTHER INFORMATION: Any amino acid

<400> SEQUENCE: 61

Trp Ser Xaa Trp Ser Xaa Cys Ser Xaa Xaa Cys Gly
  1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)..(11)
<223> OTHER INFORMATION: Any amino acid

<400> SEQUENCE: 62

Trp Ser Xaa Trp Ser Xaa Cys Ser Xaa Xaa Xaa Cys Gly
  1               5                   10
```

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)..(12)
<223> OTHER INFORMATION: Any amino acid

<400> SEQUENCE: 63

Trp Ser Xaa Trp Ser Xaa Cys Ser Xaa Xaa Xaa Xaa Cys Gly
 1               5                  10

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)..(13)
<223> OTHER INFORMATION: Any amino acid

<400> SEQUENCE: 64

Trp Ser Xaa Trp Ser Xaa Cys Ser Xaa Xaa Xaa Xaa Xaa Cys Gly
 1               5                  10                  15

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)
<223> OTHER INFORMATION: Any amino acid

<400> SEQUENCE: 65

Trp Ser Xaa Cys Ser Arg Ser Cys Gly
 1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic peptide

```
<220> FEATURE:
<221> NAME/KEY: MOD_RES
<222> LOCATION: (3)
<223> OTHER INFORMATION: Any amino acid

<400> SEQUENCE: 66

Trp Ser Xaa Cys Ser Val Ser Cys Gly
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Any amino acid

<400> SEQUENCE: 67

Trp Ser Xaa Cys Ser Val Thr Cys Gly
 1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 68

Trp Ser Xaa Xaa Cys Ser Arg Ser Cys Gly
 1               5                  10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 69

Trp Ser Xaa Xaa Cys Ser Val Ser Cys Gly
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 70
```

Trp Ser Xaa Xaa Cys Ser Val Thr Cys Gly
 1               5                  10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid

<400> SEQUENCE: 71

Trp Ser Xaa Xaa Xaa Cys Ser Arg Ser Cys Gly
 1               5                  10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid

<400> SEQUENCE: 72

Trp Ser Xaa Xaa Xaa Cys Ser Val Ser Cys Gly
 1               5                  10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid

<400> SEQUENCE: 73

Trp Ser Xaa Xaa Xaa Cys Ser Val Thr Cys Gly
 1               5                  10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid

<400> SEQUENCE: 74

Trp Ser Xaa Xaa Xaa Xaa Cys Ser Arg Ser Cys Gly
 1               5                  10

<210> SEQ ID NO 75
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid

<400> SEQUENCE: 75

Trp Ser Xaa Xaa Xaa Xaa Cys Ser Val Ser Cys Gly
 1               5                  10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid

<400> SEQUENCE: 76

Trp Ser Xaa Xaa Xaa Xaa Cys Ser Val Thr Cys Gly
 1               5                  10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid

<400> SEQUENCE: 77

Trp Ser Xaa Xaa Xaa Xaa Xaa Cys Ser Arg Ser Cys Gly
 1               5                  10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid

<400> SEQUENCE: 78

Trp Ser Xaa Xaa Xaa Xaa Xaa Cys Ser Val Ser Cys Gly
 1               5                  10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
```

```
<223> OTHER INFORMATION: Any amino acid

<400> SEQUENCE: 79

Trp Ser Xaa Xaa Xaa Xaa Xaa Cys Ser Val Thr Cys Gly
  1               5                  10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (5)..(6)
<223> OTHER INFORMATION: Gly, Ser or Cys

<400> SEQUENCE: 80

Trp Ser Xaa Trp Xaa Xaa Cys Ser Arg Ser Cys Gly
  1               5                  10

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Ser Pro Cys Ser Arg Ser Cys Gly
  1               5

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (5)..(6)
<223> OTHER INFORMATION: Gly, Ser or Cys

<400> SEQUENCE: 82

Trp Ser Xaa Trp Xaa Xaa Cys Ser Val Ser Cys Gly
  1               5                  10

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Trp Ser Pro Cys Ser Val Ser Cys Gly
  1               5
```

```
<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (5)..(6)
<223> OTHER INFORMATION: Gly, Ser or Cys

<400> SEQUENCE: 84

Trp Ser Xaa Trp Xaa Xaa Cys Ser Val Thr Cys Gly
 1               5                  10

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Ser Pro Cys Ser Val Thr Cys Gly
 1               5

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys

<400> SEQUENCE: 86

Trp Ser Xaa Trp Ser Xaa Cys Ser Arg Ser Cys Gly
 1               5                  10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys

<400> SEQUENCE: 87

Trp Ser Xaa Trp Ser Xaa Cys Ser Val Ser Cys Gly
 1               5                  10
```

```
<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys

<400> SEQUENCE: 88

Trp Ser Xaa Trp Ser Xaa Cys Ser Val Thr Cys Gly
 1               5                  10

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)
<223> OTHER INFORMATION: Any amino acid

<400> SEQUENCE: 89

Trp Ser Xaa Trp Ser Xaa Cys Ser Xaa Cys Gly
 1               5                  10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)..(10)
<223> OTHER INFORMATION: Any amino acid

<400> SEQUENCE: 90

Trp Ser Xaa Trp Ser Xaa Cys Ser Xaa Xaa Cys Gly
 1               5                  10

<210> SEQ ID NO 91
<211> LENGTH: 13
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)..(11)
<223> OTHER INFORMATION: Any amino acid

<400> SEQUENCE: 91

Trp Ser Xaa Trp Ser Xaa Cys Ser Xaa Xaa Xaa Cys Gly
 1               5                  10

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)..(12)
<223> OTHER INFORMATION: Any amino acid

<400> SEQUENCE: 92

Trp Ser Xaa Trp Ser Xaa Cys Ser Xaa Xaa Xaa Xaa Cys Gly
 1               5                  10

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys
<220> FEATURE:
<221> NAME/KEY: MOD_RES
<222> LOCATION: (9)..(13)
<223> OTHER INFORMATION: Any amino acid

<400> SEQUENCE: 93

Trp Ser Xaa Trp Ser Xaa Cys Ser Xaa Xaa Xaa Xaa Xaa Cys Gly
 1               5                  10                  15

<210> SEQ ID NO 94
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys

<400> SEQUENCE: 94

Trp Ser Xaa Trp Ser Xaa Cys Ser Arg Ser Cys Gly
 1               5                  10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys

<400> SEQUENCE: 95

Trp Ser Xaa Trp Ser Xaa Cys Ser Val Ser Cys Gly
 1               5                  10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly, Ser or Cys
<220> FEATURE:
<221> NAME/KEY: MOD_RES
<222> LOCATION: (6)
<223> OTHER INFORMATION: Gly, Ser or Cys

<400> SEQUENCE: 96

Trp Ser Xaa Trp Ser Xaa Cys Ser Val Thr Cys Gly
 1               5                  10

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Any amino acid
<220> FEATURE:
```

```
<221> NAME/KEY: MOD_RES
<222> LOCATION: (11)
<223> OTHER INFORMATION: Any amino acid
<220> FEATURE:
<221> NAME/KEY: MOD_RES
<222> LOCATION: (14)..(18)
<223> OTHER INFORMATION: Any amino acid; this range may encompass 1-5
      residues or no residues at all.

<400> SEQUENCE: 97

Xaa Xaa Xaa Xaa Xaa Trp Ser Xaa Cys Ser Xaa Cys Gly Xaa Xaa Xaa
 1               5                  10                  15

Xaa Xaa

<210> SEQ ID NO 98
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (15)..(19)
<223> OTHER INFORMATION: Any amino acid; this range may encompass 1-5
      residues or no residues at all.

<400> SEQUENCE: 98

Xaa Xaa Xaa Xaa Xaa Trp Ser Xaa Cys Ser Xaa Xaa Cys Gly Xaa Xaa
 1               5                  10                  15

Xaa Xaa Xaa

<210> SEQ ID NO 99
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (11)..(13)
<223> OTHER INFORMATION: Any amino acid
<220> FEATURE:
<221> NAME/KEY: MOD_RES
<222> LOCATION: (16)..(20)
<223> OTHER INFORMATION: Any amino acid; this range may encompass 1-5
      residues or no residues at all.

<400> SEQUENCE: 99
```

```
Xaa Xaa Xaa Xaa Xaa Trp Ser Xaa Cys Ser Xaa Xaa Xaa Cys Gly Xaa
 1               5                  10                  15

Xaa Xaa Xaa Xaa
            20
```

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (11)..(14)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 100

```
Xaa Xaa Xaa Xaa Xaa Trp Ser Xaa Cys Ser Xaa Xaa Xaa Cys Gly
 1               5                  10                  15

Xaa Xaa Xaa Xaa Xaa
            20
```

<210> SEQ ID NO 101
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (11)..(15)
<223> OTHER INFORMATION: Any amino acid
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 101

```
Xaa Xaa Xaa Xaa Xaa Trp Ser Xaa Cys Ser Xaa Xaa Xaa Xaa Xaa Cys
 1               5                  10                  15

Gly Xaa Xaa Xaa Xaa Xaa
                20
```

<210> SEQ ID NO 102
<211> LENGTH: 19

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (12)
<223> OTHER INFORMATION: Any amino acid
<220> FEATURE:
<221> NAME/KEY: MOD_RES
<222> LOCATION: (15)..(19)
<223> OTHER INFORMATION: Any amino acid; this range may encompass 1-5
      residues or no residues at all.

<400> SEQUENCE: 102

Xaa Xaa Xaa Xaa Xaa Trp Ser Xaa Xaa Cys Ser Xaa Cys Gly Xaa Xaa
 1               5                  10                  15

Xaa Xaa Xaa

<210> SEQ ID NO 103
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (16)..(20)
<223> OTHER INFORMATION: Any amino acid; this range may encompass 1-5
      residues or no residues at all.

<400> SEQUENCE: 103

Xaa Xaa Xaa Xaa Xaa Trp Ser Xaa Xaa Cys Ser Xaa Xaa Cys Gly Xaa
 1               5                  10                  15

Xaa Xaa Xaa Xaa
             20

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
```

```
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 104

Xaa Xaa Xaa Xaa Xaa Trp Ser Xaa Xaa Cys Ser Xaa Xaa Xaa Cys Gly
  1               5                  10                  15

Xaa Xaa Xaa Xaa Xaa
             20

<210> SEQ ID NO 105
<211> LENGTH: 22
<212> TYPE: PRT
<213> ORGANISM: Artificial Sequence
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (12)..(15)
<223> OTHER INFORMATION: Any amino acid
<220> FEATURE:
<221> NAME/KEY: MOD_RES
<222> LOCATION: (18)..(22)
<223> OTHER INFORMATION: Any amino acid; this range may encompass 1-5
      residues or no residues at all.
<220> FEATURE:
<223> OTHER INFORMATION: Description of Artificial Sequence: Synthetic
      peptide

<400> SEQUENCE: 105

Xaa Xaa Xaa Xaa Xaa Trp Ser Xaa Xaa Cys Ser Xaa Xaa Xaa Xaa Cys
  1               5                  10                  15

Gly Xaa Xaa Xaa Xaa Xaa
             20

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
```

```
<221> NAME/KEY: MOD_RES
<222> LOCATION: (19)..(23)
<223> OTHER INFORMATION: Any amino acid; this range may encompass 1-5
      residues or no residues at all.

<400> SEQUENCE: 106

Xaa Xaa Xaa Xaa Xaa Trp Ser Xaa Xaa Cys Ser Xaa Xaa Xaa Xaa
 1               5                  10                  15

Cys Gly Xaa Xaa Xaa Xaa Xaa
            20

<210> SEQ ID NO 107
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (13)
<223> OTHER INFORMATION: Any amino acid
<220> FEATURE:
<221> NAME/KEY: MOD_RES
<222> LOCATION: (16)..(20)
<223> OTHER INFORMATION: Any amino acid; this range may encompass 1-5
      residues or no residues at all.

<400> SEQUENCE: 107

Xaa Xaa Xaa Xaa Xaa Trp Ser Xaa Xaa Xaa Cys Ser Xaa Cys Gly Xaa
 1               5                  10                  15

Xaa Xaa Xaa Xaa
            20

<210> SEQ ID NO 108
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 108

Xaa Xaa Xaa Xaa Xaa Trp Ser Xaa Xaa Xaa Cys Ser Xaa Xaa Cys Gly
 1               5                  10                  15
```

Xaa Xaa Xaa Xaa Xaa
            20

<210> SEQ ID NO 109
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 109

Xaa Xaa Xaa Xaa Xaa Trp Ser Xaa Xaa Xaa Cys Ser Xaa Xaa Xaa Cys
 1               5                  10                  15

Gly Xaa Xaa Xaa Xaa Xaa
            20

<210> SEQ ID NO 110
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (19)..(23)
<223> OTHER INFORMATION: Any amino acid; this range may encompass 1-5
      residues or no residues at all.

<400> SEQUENCE: 110

Xaa Xaa Xaa Xaa Xaa Trp Ser Xaa Xaa Xaa Cys Ser Xaa Xaa Xaa Xaa
 1               5                  10                  15

Cys Gly Xaa Xaa Xaa Xaa Xaa
            20

<210> SEQ ID NO 111
<211> LENGTH: 24
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (20)..(24)
<223> OTHER INFORMATION: Any amino acid; this range may encompass 1-5
      residues or no residues at all.

<400> SEQUENCE: 111

Xaa Xaa Xaa Xaa Xaa Trp Ser Xaa Xaa Xaa Cys Ser Xaa Xaa Xaa Xaa
 1               5                  10                  15

Xaa Cys Gly Xaa Xaa Xaa Xaa Xaa
            20

<210> SEQ ID NO 112
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (14)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 112

Xaa Xaa Xaa Xaa Xaa Trp Ser Xaa Xaa Xaa Xaa Cys Ser Xaa Cys Gly
 1               5                  10                  15

Xaa Xaa Xaa Xaa Xaa
            20

<210> SEQ ID NO 113
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
```

```
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 113

Xaa Xaa Xaa Xaa Xaa Trp Ser Xaa Xaa Xaa Xaa Cys Ser Xaa Xaa Cys
 1               5                  10                  15

Gly Xaa Xaa Xaa Xaa Xaa
            20

<210> SEQ ID NO 114
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (19)..(23)
<223> OTHER INFORMATION: Any amino acid; this range may encompass 1-5
      residues or no residues at all.

<400> SEQUENCE: 114

Xaa Xaa Xaa Xaa Xaa Trp Ser Xaa Xaa Xaa Xaa Cys Ser Xaa Xaa Xaa
 1               5                  10                  15

Cys Gly Xaa Xaa Xaa Xaa Xaa
            20

<210> SEQ ID NO 115
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (14)..(17)
<223> OTHER INFORMATION: Any amino acid
<220> FEATURE:
<221> NAME/KEY: MOD_RES
```

```
<222> LOCATION: (20)..(24)
<223> OTHER INFORMATION: Any amino acid; this range may encompass 1-5
      residues or no residues at all.

<400> SEQUENCE: 115

Xaa Xaa Xaa Xaa Xaa Trp Ser Xaa Xaa Xaa Xaa Cys Ser Xaa Xaa Xaa
 1               5                  10                  15

Xaa Cys Gly Xaa Xaa Xaa Xaa Xaa
            20

<210> SEQ ID NO 116
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (21)..(25)
<223> OTHER INFORMATION: Any amino acid; this range may encompass 1-5
      residues or no residues at all.

<400> SEQUENCE: 116

Xaa Xaa Xaa Xaa Xaa Trp Ser Xaa Xaa Xaa Xaa Cys Ser Xaa Xaa Xaa
 1               5                  10                  15

Xaa Xaa Cys Gly Xaa Xaa Xaa Xaa Xaa
            20                  25

<210> SEQ ID NO 117
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (15)
<223> OTHER INFORMATION: Any amino acid
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 117

Xaa Xaa Xaa Xaa Xaa Trp Ser Xaa Xaa Xaa Xaa Xaa Cys Ser Xaa Cys
 1               5                  10                  15
```

```
Gly Xaa Xaa Xaa Xaa Xaa
            20

<210> SEQ ID NO 118
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (19)..(23)
<223> OTHER INFORMATION: Any amino acid; this range may encompass 1-5
      residues or no residues at all.

<400> SEQUENCE: 118

Xaa Xaa Xaa Xaa Xaa Trp Ser Xaa Xaa Xaa Xaa Xaa Cys Ser Xaa Xaa
  1               5                  10                  15

Cys Gly Xaa Xaa Xaa Xaa Xaa
            20

<210> SEQ ID NO 119
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<221> NAME/KEY: MOD_RES
<222> LOCATION: (20)..(24)
<223> OTHER INFORMATION: Any amino acid; this range may encompass 1-5
      residues or no residues at all.

<400> SEQUENCE: 119

Xaa Xaa Xaa Xaa Xaa Trp Ser Xaa Xaa Xaa Xaa Xaa Cys Ser Xaa Xaa
  1               5                  10                  15

Xaa Cys Gly Xaa Xaa Xaa Xaa Xaa
            20

<210> SEQ ID NO 120
<211> LENGTH: 25
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (21)..(25)
<223> OTHER INFORMATION: Any amino acid; this range may encompass 1-5
      residues or no residues at all.

<400> SEQUENCE: 120

Xaa Xaa Xaa Xaa Xaa Trp Ser Xaa Xaa Xaa Xaa Xaa Cys Ser Xaa Xaa
 1               5                  10                  15

Xaa Xaa Cys Gly Xaa Xaa Xaa Xaa Xaa
            20                  25

<210> SEQ ID NO 121
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (15)..(19)
<223> OTHER INFORMATION: Any amino acid
<220> FEATURE:
<221> NAME/KEY: MOD_RES
<222> LOCATION: (22)..(26)
<223> OTHER INFORMATION: Any amino acid; this range may encompass 1-5
      residues or no residues at all.

<400> SEQUENCE: 121

Xaa Xaa Xaa Xaa Xaa Trp Ser Xaa Xaa Xaa Xaa Xaa Cys Ser Xaa Xaa
 1               5                  10                  15

Xaa Xaa Xaa Cys Gly Xaa Xaa Xaa Xaa Xaa
                20                  25

<210> SEQ ID NO 122
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
```

```
<222> LOCATION: (8)
<223> OTHER INFORMATION: Gly, Ser or Cys
<220> FEATURE:
<221> NAME/KEY: MOD_RES
<222> LOCATION: (10)..(11)
<223> OTHER INFORMATION: Gly, Ser or Cys
<220> FEATURE:
<221> NAME/KEY: MOD_RES
<222> LOCATION: (14)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 122

Xaa Xaa Xaa Xaa Xaa Trp Ser Xaa Trp Xaa Xaa Cys Ser Xaa Cys Gly
 1               5                  10                  15

Xaa Xaa Xaa Xaa Xaa
            20

<210> SEQ ID NO 123
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (11)
<223> OTHER INFORMATION: Any amino acid
<220> FEATURE:
<221> NAME/KEY: MOD_RES
<222> LOCATION: (14)..(18)
<223> OTHER INFORMATION: Any amino acid; this range may encompass 1-5
      residues or no residues at all.

<400> SEQUENCE: 123

Xaa Xaa Xaa Xaa Xaa Trp Ser Pro Cys Ser Xaa Cys Gly Xaa Xaa Xaa
 1               5                  10                  15

Xaa Xaa

<210> SEQ ID NO 124
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (10)..(11)
<223> OTHER INFORMATION: Gly, Ser or Cys
<220> FEATURE:
<221> NAME/KEY: MOD_RES
<222> LOCATION: (14)..(15)
<223> OTHER INFORMATION: Any amino acid
```

```
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 124

Xaa Xaa Xaa Xaa Xaa Trp Ser Xaa Trp Xaa Xaa Cys Ser Xaa Xaa Cys
  1               5                  10                  15

Gly Xaa Xaa Xaa Xaa Xaa
             20

<210> SEQ ID NO 125
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (15)..(19)
<223> OTHER INFORMATION: Any amino acid; this range may encompass 1-5
      residues or no residues at all.

<400> SEQUENCE: 125

Xaa Xaa Xaa Xaa Xaa Trp Ser Pro Cys Ser Xaa Xaa Cys Gly Xaa Xaa
  1               5                  10                  15

Xaa Xaa Xaa

<210> SEQ ID NO 126
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (10)..(11)
<223> OTHER INFORMATION: Gly, Ser or Cys
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (19)..(23)
<223> OTHER INFORMATION: Any amino acid; this range may encompass 1-5
      residues or no residues at all.

<400> SEQUENCE: 126

Xaa Xaa Xaa Xaa Xaa Trp Ser Xaa Trp Xaa Xaa Cys Ser Xaa Xaa Xaa
  1               5                  10                  15
```

```
Cys Gly Xaa Xaa Xaa Xaa Xaa
            20
```

<210> SEQ ID NO 127
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (11)..(13)
<223> OTHER INFORMATION: Any amino acid
<220> FEATURE:
<221> NAME/KEY: MOD_RES
<222> LOCATION: (16)..(20)
<223> OTHER INFORMATION: Any amino acid; this range may encompass 1-5
      residues or no residues at all.

<400> SEQUENCE: 127

```
Xaa Xaa Xaa Xaa Xaa Trp Ser Pro Cys Ser Xaa Xaa Xaa Cys Gly Xaa
 1               5                  10                  15

Xaa Xaa Xaa Xaa
            20
```

<210> SEQ ID NO 128
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (10)..(11)
<223> OTHER INFORMATION: Gly, Ser or Cys
<220> FEATURE:
<221> NAME/KEY: MOD_RES
<222> LOCATION: (14)..(17)
<223> OTHER INFORMATION: Any amino acid
<220> FEATURE:
<221> NAME/KEY: MOD_RES
<222> LOCATION: (20)..(24)
<223> OTHER INFORMATION: Any amino acid; this range may encompass 1-5
      residues or no residues at all.

<400> SEQUENCE: 128

```
Xaa Xaa Xaa Xaa Xaa Trp Ser Xaa Trp Xaa Xaa Cys Ser Xaa Xaa Xaa
 1               5                  10                  15

Xaa Cys Gly Xaa Xaa Xaa Xaa Xaa
            20
```

<210> SEQ ID NO 129
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (11)..(14)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 129

Xaa Xaa Xaa Xaa Xaa Trp Ser Pro Cys Ser Xaa Xaa Xaa Xaa Cys Gly
  1               5                  10                  15

Xaa Xaa Xaa Xaa Xaa
             20

<210> SEQ ID NO 130
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (10)..(11)
<223> OTHER INFORMATION: Gly, Ser or Cys
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (21)..(25)
<223> OTHER INFORMATION: Any amino acid; this range may encompass 1-5
      residues or no residues at all.

<400> SEQUENCE: 130

Xaa Xaa Xaa Xaa Xaa Trp Ser Xaa Trp Xaa Xaa Cys Ser Xaa Xaa Xaa
  1               5                  10                  15

Xaa Xaa Cys Gly Xaa Xaa Xaa Xaa Xaa
             20                  25

<210> SEQ ID NO 131
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
```

```
<221> NAME/KEY: MOD_RES
<222> LOCATION: (11)..(15)
<223> OTHER INFORMATION: Any amino acid
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 131

Xaa Xaa Xaa Xaa Xaa Trp Ser Pro Cys Ser Xaa Xaa Xaa Xaa Xaa Cys
 1               5                  10                  15

Gly Xaa Xaa Xaa Xaa Xaa
            20

<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (14)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 132

Xaa Xaa Xaa Xaa Xaa Trp Ser Xaa Trp Ser Xaa Cys Ser Xaa Cys Gly
 1               5                  10                  15

Xaa Xaa Xaa Xaa Xaa
            20

<210> SEQ ID NO 133
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
```

```
<222> LOCATION: (14)..(15)
<223> OTHER INFORMATION: Any amino acid
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 133

Xaa Xaa Xaa Xaa Xaa Trp Ser Xaa Trp Ser Xaa Cys Ser Xaa Xaa Cys
 1               5                  10                  15

Gly Xaa Xaa Xaa Xaa Xaa
            20

<210> SEQ ID NO 134
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (19)..(23)
<223> OTHER INFORMATION: Any amino acid; this range may encompass 1-5
      residues or no residues at all.

<400> SEQUENCE: 134

Xaa Xaa Xaa Xaa Xaa Trp Ser Xaa Trp Ser Xaa Cys Ser Xaa Xaa Xaa
 1               5                  10                  15

Cys Gly Xaa Xaa Xaa Xaa Xaa
            20

<210> SEQ ID NO 135
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (14)..(17)
```

```
<223> OTHER INFORMATION: Any amino acid
<220> FEATURE:
<221> NAME/KEY: MOD_RES
<222> LOCATION: (20)..(24)
<223> OTHER INFORMATION: Any amino acid; this range may encompass 1-5
      residues or no residues at all.

<400> SEQUENCE: 135

Xaa Xaa Xaa Xaa Xaa Trp Ser Xaa Trp Ser Xaa Cys Ser Xaa Xaa Xaa
 1               5                  10                  15

Xaa Cys Gly Xaa Xaa Xaa Xaa Xaa
            20

<210> SEQ ID NO 136
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (21)..(25)
<223> OTHER INFORMATION: Any amino acid; this range may encompass 1-5
      residues or no residues at all.

<400> SEQUENCE: 136

Xaa Xaa Xaa Xaa Xaa Trp Ser Xaa Trp Ser Xaa Cys Ser Xaa Xaa Xaa
 1               5                  10                  15

Xaa Xaa Cys Gly Xaa Xaa Xaa Xaa Xaa
            20                  25

<210> SEQ ID NO 137
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (15)..(19)
<223> OTHER INFORMATION: Any amino acid; this range may encompass 1-5
      residues or no residues at all.

<400> SEQUENCE: 137
```

```
Xaa Xaa Xaa Xaa Xaa Trp Ser Xaa Cys Ser Arg Ser Cys Gly Xaa Xaa
 1               5              10                  15

Xaa Xaa Xaa

<210> SEQ ID NO 138
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (15)..(19)
<223> OTHER INFORMATION: Any amino acid; this range may encompass 1-5
      residues or no residues at all.

<400> SEQUENCE: 138

Xaa Xaa Xaa Xaa Xaa Trp Ser Xaa Cys Ser Val Ser Cys Gly Xaa Xaa
 1               5              10                  15

Xaa Xaa Xaa

<210> SEQ ID NO 139
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (15)..(19)
<223> OTHER INFORMATION: Any amino acid; this range may encompass 1-5
      residues or no residues at all.

<400> SEQUENCE: 139

Xaa Xaa Xaa Xaa Xaa Trp Ser Xaa Cys Ser Val Thr Cys Gly Xaa Xaa
 1               5              10                  15

Xaa Xaa Xaa

<210> SEQ ID NO 140
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
```

```
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (16)..(20)
<223> OTHER INFORMATION: Any amino acid; this range may encompass 1-5
      residues or no residues at all.

<400> SEQUENCE: 140

Xaa Xaa Xaa Xaa Xaa Trp Ser Xaa Xaa Cys Ser Arg Ser Cys Gly Xaa
 1               5                  10                  15

Xaa Xaa Xaa Xaa
            20

<210> SEQ ID NO 141
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (16)..(20)
<223> OTHER INFORMATION: Any amino acid; this range may encompass 1-5
      residues or no residues at all.

<400> SEQUENCE: 141

Xaa Xaa Xaa Xaa Xaa Trp Ser Xaa Xaa Cys Ser Val Ser Cys Gly Xaa
 1               5                  10                  15

Xaa Xaa Xaa Xaa
            20

<210> SEQ ID NO 142
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (16)..(20)
<223> OTHER INFORMATION: Any amino acid; this range may encompass 1-5
      residues or no residues at all.

<400> SEQUENCE: 142

Xaa Xaa Xaa Xaa Xaa Trp Ser Xaa Xaa Cys Ser Val Thr Cys Gly Xaa
 1               5                  10                  15

Xaa Xaa Xaa Xaa
            20
```

```
<210> SEQ ID NO 143
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 143

Xaa Xaa Xaa Xaa Xaa Trp Ser Xaa Xaa Xaa Cys Ser Arg Ser Cys Gly
 1               5                  10                  15

Xaa Xaa Xaa Xaa Xaa
            20

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 144

Xaa Xaa Xaa Xaa Xaa Trp Ser Xaa Xaa Xaa Cys Ser Val Ser Cys Gly
 1               5                  10                  15

Xaa Xaa Xaa Xaa Xaa
            20

<210> SEQ ID NO 145
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(10)
<223> OTHER INFORMATION: Any amino acid
```

```
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 145

Xaa Xaa Xaa Xaa Xaa Trp Ser Xaa Xaa Xaa Cys Ser Val Thr Cys Gly
 1               5                  10                  15

Xaa Xaa Xaa Xaa Xaa
            20

<210> SEQ ID NO 146
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (17)..(22)
<223> OTHER INFORMATION: Any amino acid; this range may encompass 1-5
      residues or no residues at all.

<400> SEQUENCE: 146

Xaa Xaa Xaa Xaa Xaa Trp Ser Xaa Xaa Xaa Xaa Cys Ser Arg Ser Cys
 1               5                  10                  15

Gly Xaa Xaa Xaa Xaa Xaa
            20

<210> SEQ ID NO 147
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 147

Xaa Xaa Xaa Xaa Xaa Trp Ser Xaa Xaa Xaa Xaa Cys Ser Val Ser Cys
 1               5                  10                  15

Gly Xaa Xaa Xaa Xaa Xaa
            20

<210> SEQ ID NO 148
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(11)
<223> OTHER INFORMATION: Any amino acid
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 148

Xaa Xaa Xaa Xaa Xaa Trp Ser Xaa Xaa Xaa Xaa Cys Ser Val Thr Cys
 1               5                  10                  15

Gly Xaa Xaa Xaa Xaa Xaa
            20

<210> SEQ ID NO 149
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (19)..(23)
<223> OTHER INFORMATION: Any amino acid; this range may encompass 1-5
      residues or no residues at all.

<400> SEQUENCE: 149

Xaa Xaa Xaa Xaa Xaa Trp Ser Xaa Xaa Xaa Xaa Xaa Cys Ser Arg Ser
 1               5                  10                  15

Cys Gly Xaa Xaa Xaa Xaa Xaa
            20

<210> SEQ ID NO 150
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (19)..(23)
```

```
<223> OTHER INFORMATION: Any amino acid; this range may encompass 1-5
      residues or no residues at all.

<400> SEQUENCE: 150

Xaa Xaa Xaa Xaa Xaa Trp Ser Xaa Xaa Xaa Xaa Xaa Cys Ser Val Ser
 1               5                  10                  15

Cys Gly Xaa Xaa Xaa Xaa Xaa
            20

<210> SEQ ID NO 151
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (19)..(23)
<223> OTHER INFORMATION: Any amino acid; this range may encompass 1-5
      residues or no residues at all.

<400> SEQUENCE: 151

Xaa Xaa Xaa Xaa Xaa Trp Ser Xaa Xaa Xaa Xaa Xaa Cys Ser Val Thr
 1               5                  10                  15

Cys Gly Xaa Xaa Xaa Xaa Xaa
            20

<210> SEQ ID NO 152
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (10)..(11)
<223> OTHER INFORMATION: Gly, Ser or Cys
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 152

Xaa Xaa Xaa Xaa Xaa Trp Ser Xaa Trp Xaa Xaa Cys Ser Arg Ser Cys
 1               5                  10                  15

Gly Xaa Xaa Xaa Xaa Xaa
            20

<210> SEQ ID NO 153
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (15)..(19)
<223> OTHER INFORMATION: Any amino acid; this range may encompass 1-5
      residues or no residues at all.

<400> SEQUENCE: 153

Xaa Xaa Xaa Xaa Xaa Trp Ser Pro Cys Ser Arg Ser Cys Gly Xaa Xaa
 1               5                  10                  15

Xaa Xaa Xaa

<210> SEQ ID NO 154
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (10)..(11)
<223> OTHER INFORMATION: Gly, Ser or Cys
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 154

Xaa Xaa Xaa Xaa Xaa Trp Ser Xaa Trp Xaa Xaa Cys Ser Val Ser Cys
 1               5                  10                  15

Gly Xaa Xaa Xaa Xaa Xaa
            20

<210> SEQ ID NO 155
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (15)..(19)
<223> OTHER INFORMATION: Any amino acid; this range may encompass 1-5
      residues or no residues at all.

<400> SEQUENCE: 155
```

Xaa Xaa Xaa Xaa Xaa Trp Ser Pro Cys Ser Val Ser Cys Gly Xaa Xaa
 1               5                  10                  15

Xaa Xaa Xaa

<210> SEQ ID NO 156
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (10)..(11)
<223> OTHER INFORMATION: Gly, Ser or Cys
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 156

Xaa Xaa Xaa Xaa Xaa Trp Ser Xaa Trp Xaa Xaa Cys Ser Val Thr Cys
 1               5                  10                  15

Gly Xaa Xaa Xaa Xaa Xaa
            20

<210> SEQ ID NO 157
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (15)..(19)
<223> OTHER INFORMATION: Any amino acid; this range may encompass 1-5
      residues or no residues at all.

<400> SEQUENCE: 157

Xaa Xaa Xaa Xaa Xaa Trp Ser Pro Cys Ser Val Thr Cys Gly Xaa Xaa
 1               5                  10                  15

Xaa Xaa Xaa

<210> SEQ ID NO 158
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5

```
        residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (18)..(22)
<223> OTHER INFORMATION: Any amino acid; this range may encompass 1-5
        residues or no residues at all.

<400> SEQUENCE: 158

Xaa Xaa Xaa Xaa Xaa Trp Ser Xaa Trp Ser Xaa Cys Ser Arg Ser Cys
 1               5                  10                  15

Gly Xaa Xaa Xaa Xaa Xaa
            20

<210> SEQ ID NO 159
<211> LENGTH: 22
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(5)
<223> OTHER INFORMATION: Any amino acid; this range may encompass 1-5
        residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (18)..(22)
<223> OTHER INFORMATION: Any amino acid; this range may encompass 1-5
        residues or no residues at all.

<400> SEQUENCE: 159

Xaa Xaa Xaa Xaa Xaa Trp Ser Xaa Trp Ser Xaa Cys Ser Val Ser Cys
 1               5                  10                  15

Gly Xaa Xaa Xaa Xaa Xaa
            20

<210> SEQ ID NO 160
<211> LENGTH: 22
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(5)
<223> OTHER INFORMATION: Any amino acid; this range may encompass 1-5
        residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
```

```
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 160

Xaa Xaa Xaa Xaa Xaa Trp Ser Xaa Trp Ser Xaa Cys Ser Val Thr Cys
 1               5                  10                  15

Gly Xaa Xaa Xaa Xaa Xaa
            20

<210> SEQ ID NO 161
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (14)
<223> OTHER INFORMATION: Any amino acid
<220> FEATURE:
<221> NAME/KEY: MOD_RES
<222> LOCATION: (17)..(21)
<223> OTHER INFORMATION: Any amino acid; this range may encompass 1-5
      residues or no residues at all.

<400> SEQUENCE: 161

Xaa Xaa Xaa Xaa Xaa Trp Ser Xaa Trp Ser Xaa Cys Ser Xaa Cys Gly
 1               5                  10                  15

Xaa Xaa Xaa Xaa Xaa
            20

<210> SEQ ID NO 162
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (14)..(15)
<223> OTHER INFORMATION: Any amino acid
<220> FEATURE:
```

```
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 162

Xaa Xaa Xaa Xaa Xaa Trp Ser Xaa Trp Ser Xaa Cys Ser Xaa Xaa Cys
 1               5                  10                  15

Gly Xaa Xaa Xaa Xaa Xaa
            20

<210> SEQ ID NO 163
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (19)..(23)
<223> OTHER INFORMATION: Any amino acid; this range may encompass 1-5
      residues or no residues at all.

<400> SEQUENCE: 163

Xaa Xaa Xaa Xaa Xaa Trp Ser Xaa Trp Ser Xaa Cys Ser Xaa Xaa Xaa
 1               5                  10                  15

Cys Gly Xaa Xaa Xaa Xaa Xaa
            20

<210> SEQ ID NO 164
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (14)..(17)
<223> OTHER INFORMATION: Any amino acid
<220> FEATURE:
<221> NAME/KEY: MOD_RES
```

```
-continued

<222> LOCATION: (20)..(24)
<223> OTHER INFORMATION: Any amino acid; this range may encompass 1-5
      residues or no residues at all.

<400> SEQUENCE: 164

Xaa Xaa Xaa Xaa Xaa Trp Ser Xaa Trp Ser Xaa Cys Ser Xaa Xaa Xaa
 1               5                  10                  15

Xaa Cys Gly Xaa Xaa Xaa Xaa Xaa
            20

<210> SEQ ID NO 165
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (21)..(25)
<223> OTHER INFORMATION: Any amino acid; this range may encompass 1-5
      residues or no residues at all.

<400> SEQUENCE: 165

Xaa Xaa Xaa Xaa Xaa Trp Ser Xaa Trp Ser Xaa Cys Ser Xaa Xaa Xaa
 1               5                  10                  15

Xaa Xaa Cys Gly Xaa Xaa Xaa Xaa Xaa
            20                  25

<210> SEQ ID NO 166
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 166
```

```
Xaa Xaa Xaa Xaa Xaa Trp Ser Xaa Trp Ser Xaa Cys Ser Arg Ser Cys
 1               5                  10                  15

Gly Xaa Xaa Xaa Xaa Xaa
            20
```

<210> SEQ ID NO 167
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 167

```
Xaa Xaa Xaa Xaa Xaa Trp Ser Xaa Trp Ser Xaa Cys Ser Val Ser Cys
 1               5                  10                  15

Gly Xaa Xaa Xaa Xaa Xaa
            20
```

<210> SEQ ID NO 168
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid; this range may encompass 1-5
      residues or no residues at all.
<220> FEATURE:
<221> NAME/KEY: MOD_RES
<222> LOCATION: (8)
<223> OTHER INFORMATION: Gly, Ser or Cys
<220> FEATURE:
<221> NAME/KEY: MOD_RES
<222> LOCATION: (11)
<223> OTHER INFORMATION: Gly, Ser or Cys
<220> FEATURE:
<221> NAME/KEY: MOD_RES
<222> LOCATION: (18)..(22)
<223> OTHER INFORMATION: Any amino acid; this range may encompass 1-5
      residues or no residues at all.

<400> SEQUENCE: 168

```
Xaa Xaa Xaa Xaa Xaa Trp Ser Xaa Trp Ser Xaa Cys Ser Val Thr Cys
 1               5                  10                  15

Gly Xaa Xaa Xaa Xaa Xaa
            20
```